US012558295B2

(12) United States Patent
Clark et al.

(10) Patent No.: US 12,558,295 B2
(45) Date of Patent: Feb. 24, 2026

(54) ORAL POUCH

(71) Applicants:Brendan Edward Clark, Rocky River, OH (US); Ronald Charles Krosky, Sparks Glencoe, MD (US)

(72) Inventors: Brendan Edward Clark, Rocky River, OH (US); Ronald Charles Krosky, Sparks Glencoe, MD (US)

( * ) Notice: Subject to any disclaimer, the term of this patent is extended or adjusted under 35 U.S.C. 154(b) by 285 days.

(21) Appl. No.: 18/466,736

(22) Filed: Sep. 13, 2023

(65) Prior Publication Data

US 2024/0091108 A1      Mar. 21, 2024

Related U.S. Application Data

(60) Provisional application No. 63/376,088, filed on Sep. 17, 2022.

(51) Int. Cl.
| | |
|---|---|
| *A61K 8/02* | (2006.01) |
| *A24B 13/00* | (2006.01) |
| *A24B 15/16* | (2020.01) |
| *A61Q 11/00* | (2006.01) |

(52) U.S. Cl.
CPC ............ *A61K 8/0204* (2013.01); *A24B 13/00* (2013.01); *A24B 15/16* (2013.01); *A61Q 11/00* (2013.01); *A61K 2800/92* (2013.01)

(58) Field of Classification Search
CPC .. A61K 8/0204; A61K 2800/92; A24B 13/00; A24B 15/16; A61Q 11/00
See application file for complete search history.

(56) References Cited

U.S. PATENT DOCUMENTS

| | | | |
|---|---|---|---|
| 9,402,810 B2 | 8/2016 | Nilsson | |
| 9,687,639 B1 | 6/2017 | Krosky et al. | |
| 2004/0219190 A1* | 11/2004 | Kosti | A61K 8/0208 424/62 |
| 2016/0157515 A1 | 6/2016 | Chapman et al. | |
| 2017/0098059 A1 | 4/2017 | Krosky et al. | |
| 2018/0344996 A1 | 12/2018 | Krosky et al. | |
| 2022/0322727 A1 | 10/2022 | Stahl et al. | |

FOREIGN PATENT DOCUMENTS

| | | | | |
|---|---|---|---|---|
| EP | 3192380 | * | 7/2017 | A24B 13/00 |
| WO | WO 2021/053078 | * | 3/2021 | |
| WO | WO 2012/220898 | * | 11/2021 | A24B 15/42 |

OTHER PUBLICATIONS

Mouthrinse (Mouthwash) | American Dental Association, available at https://www.ada.org/resources/research/science-and-research-institute/oral-health-topics/mouthrinse-mouthwash#:~: text= Antimicrobials%20in%20mouthrinse%20formulations% 20include,ketone%2C%20terpene%2C%20and%20ionone.
Our Ingredients: What's in your Listerine (R) Mouthwash?, available at https://www.listerine.com/our-sustainability/ingredients.
Sadoogh-Abasian, F. and Evered, D. F. Absorption of vitamin C from the human buccal cavity. Available at https://pubmed.ncbi. nlm.nih.gov/486391/ (Jul. 1979).
Avena, Nicole. What You Need to Know about Sublingual Vitamins. https://www.psychologytoday.com/US/blog/food-junkie/201810/ what-you-need-know-about-sublingual-vitamins#:~:text=Sublingual% 20vitamins%2C%20which%20are%20meant,vitamins%20have% 20many%20other%20benefits (Oct. 18, 2018).
Sublingual Administration—Wikipedia, available at https://en. wikipedia.org/wiki/Sublingual_administration.
Buccal Administration—Wikipedia, available at https://en.wikipedia. org/wiki/Buccal_administration.
Sublabial administration—Wikipedia, available at https://en.wikipedia. org/wiki/Sublabial_administration.
Chewing Gum May Be Effective for Delivering Vitamins—Science Daily, available at https://www.sciencedaily.com/releases/2018/10/ 181010105610.htm#:~:text=Lambert%20and%20colleagues% 20found%20that,who%20chewed%20the%20supplemented% 20gums.
Feliz-Matos, Leandro, Hernandez, Luis Miguel, Abreau, Ninoska. Dental Bleaching Techniques; Hydrogen-carbamide Peroxides and Light Sources for Activation, an Update. Mini Review Article. https://www.ncbi.nlm.nih.gov/pmc/articles/PMC4311381/ (Jan. 6, 2015).
Benowitz, et al. Nicotine Chemistry, Metabolism, Kinetics and Biomarkers. Available at https://www.ncbi.nlm.nih.gov/pmc/articles/ PMC2953858/#:~:text=Absorption%20of%20nicotine%20across% 20biological,(pH%205.5%E2%80%936.0) (Oct. 13, 2010).
Marchant-Turner, Renee. Remineralization confusion . . . runs rampant in my mind. Where do I begin? https://www.rdhmag.com/ patient-care/rinses-pastes/article/16404924/remineralization-confusion- runs-rampant-in-my-mind-where-do-i-begin (Dec. 1, 2009).
Dexter, Amanda. Review of Non-Peroxide Teeth Whitening Alter- natives and Solutions. https://www.dentaly.org/us/teeth-whitening/ non-peroxide/ (Jun. 9, 2023).
Engler, Alexandra. The 8 Best Natural & Nontoxic Teeth-Whitening Products. https://www.mindbodygreen.com/articles/the-best-natural- and-nontoxic-teeth-brightening-products (Apr. 14, 2022).
Malin, Zoe. 7 best ADA-accepted whitening toothpastes of 2023. https://www.nbcnews.com/select/shopping/best-whitening-toothpaste- ncna1294908 (Apr. 29, 2022).

* cited by examiner

*Primary Examiner* — Shirley V Gembeh

(57) ABSTRACT

Pouches are disclosed that can incorporate components in addition to consumables such as nicotine. Such components can include tooth whitening substances, oral antiseptics, gum or tooth health substances, vitamins, medicaments, and others. Such components can be provided within a pouch with the consumable, be impregnated into a pouch material, or be coated onto a pouch.

11 Claims, 10 Drawing Sheets

1100

ORAL POUCH

CROSS-REFERENCE TO RELATED APPLICATION

This application claims priority to and the benefit of U.S. Provisional Application No. 63/376,088, filed Sep. 17, 2022 and titled "Oral Pouch," the entirety of which is incorporated herein by reference.

FIELD

This disclosure concerns orally-held pouches, such as those containing nicotine, and particularly pouches designed to provide a beneficial health effect to the user.

BACKGROUND

The popularity of "pouch" nicotine products (as well as pouches with nicotine substitutes or other materials) has increased steadily in recent years. Pouches on the market contain, for example. tobacco, nicotine other than from tobacco (e.g., nicotine salts), and dozens of companies offer different varieties of such pouches. Some companies offer reduced nicotine pouches or non-nicotine pouches (containing, e.g., coffee) to provide less harmful alternatives, or mechanisms for quitting, to consumers who habitually use oral nicotine products.

Despite increased offerings, there are many health and aesthetic downsides to "dipping" (with or without a pouch) and other oral practices. For example, using oral tobacco, drinking coffee, and drinking red wine can individually or collectively stain teeth. Delivering a beneficial substance concurrent or independent of these types of actions has to date been missed.

SUMMARY

Pouches (and other delivery or storage mechanisms) are disclosed that can incorporate components in addition to consumables (such as nicotine). Such components can include health products or other substances, such as tooth whitening substances, oral antiseptics, gum or tooth health substances, vitamins, medicaments, and others. Such components can be provided within a pouch with the consumable, be impregnated into a pouch material, be coated onto a pouch, or be stored in a compartment or partition of a pouch at least partially isolated from another section. Alternatively or complementarily, pouches can contain nested pouches.

The summary is intended to describe a subset of embodiments disclosed herein and should not be interpreted to limit any alternative or complementary details set forth hereafter.

Figure 1:
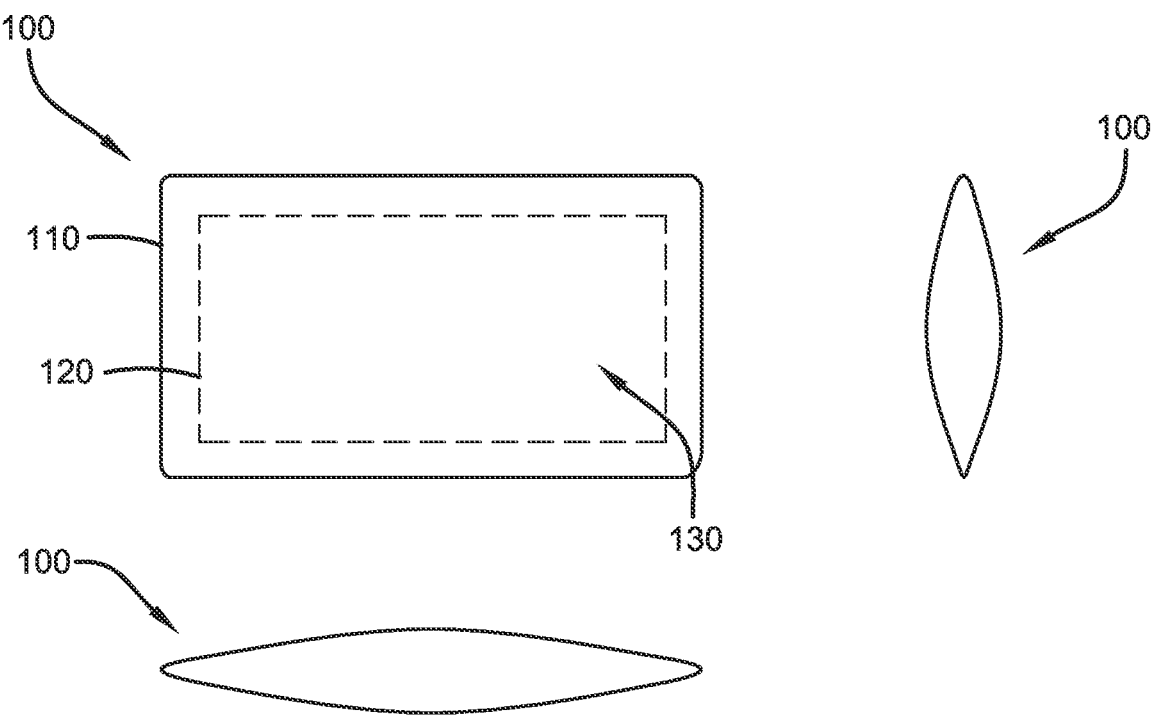
FIG. 1 illustrates an example pouch structure.

The drawings are intended to illustrate a subset of embodiments disclosed herein and should not be interpreted to limit any alternative or complementary details set forth hereafter.

DETAILED DESCRIPTION

Many people utilize products held in the mouth, such as oral tobacco. These products come in a variety of forms including pouches (as distinguished from, e.g., snuff or long cut tobacco or substitutes). Pouches provide the user a "dipping" experience without the mess of loose tobacco, grounds, et cetera. However, pouch users only receive a fraction of the benefits that could be delivered by pouches. In addition to providing nicotine, caffeine, flavor, or other pouch-delivered substances, this disclosure describes supplementing pouch content with other substances to add health benefits. Many regard "dipping" or "chewing" as unhealthy. The embodiments herein can improve user health, and may offset some of the negative effects of these tobacco and other oral practices.

For example, many people suffer from stained teeth. Many of these people are nicotine users—either cigarettes or loose oral tobacco—and utilize nicotine pouches as a way to avoid some of the harmful ingredients in other tobacco products or to control their nicotine intake in an effort to reduce usage. Many people, including but not limited to users of oral tobacco, desire to undo tooth staining. Thus, there is a need to provide tooth whitening options to the tobacco-using community. Coffee drinkers also frequently have stained teeth. Many people in the population generally have stained teeth. Such people would benefit from the incorporation of tooth-whitening substances in pouches that they use. As used herein, a tooth-whitening substance can include, but is not limited to, hydrogen peroxide, carbamide peroxide, magnesium peroxide, calcium peroxide, other peroxides (any peroxides herein can be concentrated from 0% (trace amounts) to 40% or more), amino acids, bleach-based whitening agents (e.g., bleaching gels, bleaching powders), sodium bicarbonate, remineralizing substances, colorants or dyes, abrasives (e.g., hydrated silica, perlite, alumina, activated charcoal, ash, other silicas), antiredeposition agents (e.g., polyphosphates, sodium citrate), calcium phosphates e.g hydroxyapatite), blue covarine or similar substances, polyaspartate (e.g., sodium polyaspartate), surfactants (e.g., sodium lauryl sulfate), whitening wash formulations (containing, e.g., non-acidic vitamin C, aloe vera, coconut oil, mint, tea tree extracts, sage), pulling oils (e.g., coconut oil, sesame oil, sunflower oil, lemon peel oil, black seed oil, tea tree oil, essential oils), phthalimidoperoxycaproic acid (PAP), or others known in the art, or combinations thereof.

In embodiments substances can be included to reduce tooth, gum, or other oral sensitivity (e.g., numbing or desensitizing agents) and/or provide other benefits (e.g., fluoride, potassium citrate). Other such substances that can be combined with consumables or used to treat a pouch can include but are not limited to, e.g., HEMA, glutaraldehyde, red propolis extract, calcium sodium phosphosilicate, and arginine-calcium carbonate, amorphous calcium phosphate, casein phosphopeptide, or combinations thereof.

Many substances can be absorbed through the mouth, gums, throat, et cetera, i.e., bucally, sublabially, or sublingually. Therefore it is beneficial to provide health-improving substances—vitamins, minerals, medicaments, et cetera—in pouches including other materials. Vitamins absorbed through the mouth or gums include vitamins A1, B1, B2, B3, B6, B9, B12, C, and E. Other substances such as glucose gel can be absorbed bucally, sublabially, and/or sublingually. Additionally, herbal or other remedies or supplements can be provided through the pouch (e.g., delivery of *Hypericum perforatum*, commonly referred to as "St. John's wort"). Other products benefitting health but not specifically benefitting mouth, teeth, gums, throat, et cetera, such as, e.g., antioxidants or probiotics can also be incorporated into a pouch herein as a consumable or treatment.

Various medicines can also be absorbed in such manners. In one example, a patient can be unconscious and found by emergency or other medical personnel. The emergency personnel can place a pouch into the mouth of the unconscious patient to quickly administer medicine in a relatively controlled manner. Users can in alternative examples self-administer or administer to conscious people. Example medicines can include, as examples, cardiovascular drugs, steroids, psychiatric drugs (e.g., asenapine), antidepressants, aspirin, opioids (e.g., fentanyl, buprenorphine, naloxone), anticonvulsants (e.g., midazolam), glyceryl trinitrate, nitroglycerine, prochlorperazine, testosterone, tetrahydrocannabinol ("THC"), cannabidiol ("CBD"), barbiturates, and benzodiazepines. These medicines can be used for overall health benefits (e.g. the cardiovascular drugs), comfort benefits (e.g., opioids to counteract painful emergency lifesaving procedures), or other purposes (e.g., a trial delivery method for an antidepressant).

Additional materials that can be beneficial to introduce to the mouth, gums, tongue, et cetera—as is done when using oral pouches—include, e.g., substances for gum, tooth, or mouth health, oral antisepetics or mouthwashes/mouth rinses, and others. These can, e.g., improve breath, impede the development of plaque or tartar, support enamel, reduce bacteria, resist staining, promote health in receding gums, et cetera. Examples of materials that can be utilized with pouches can include antacids or pH-balancing substances, eucalyptol, menthol, methyl salicylate, ethanol or other alcohols, thymol, sorbitol, sodium benzoate, benzoic acid, poloxamer 407, zinc chloride, chlorhexidine, fluoride, cetylpyridinium chloride, xylitol, propolis, triclosan, zinc, sodium chloride, hexetidine, cetylpyridinium, chlorine dioxide, et cetera. Many users spit out saliva that accumulates during pouch use. As such, the types of substances, amounts of substances, concentration of substances, et cetera, can be provided in or with a pouch based on an understanding that materials therein will be absorbed bucally/sublabially/sublingually, and/or not swallowed. Moreover, as discussed, certain consumables or supplements may interact in a manner that counteracts the full effects or reduces the amount of a substance delivered. Alternatively, some combinations may enhance effects. As such, the amounts or concentrations of substances provided can be calibrated to provide appropriate uptake and/or experience. For example, a user may typically use a 2 mg nicotine pouch. A pouch may be provided with a weakly acidic tooth whitening substance. As such, the amount of nicotine can be increased to provide a "2 mg equivalent" with tooth whitening properties, allowing the user to have a similar experience while absorbing nicotine at a slower rate. Alternatively, a supplement may enhance the user experience of THC, and so the THC amount or concentration may be reduced to provide the consistent, expected experience.

Certain materials may be better absorbed by the human body under certain conditions. For example, at least some forms of nicotine cross membranes in a basic environment. Substances can be added to pouches to create a better environment for consumable absorption. Moreover, consumables or supplements may reduce the efficacy of one another. Continuing with the prior example, some tooth whitening products (e.g., peroxide based) may be weak acids that could reduce absorption or degrade products or experience. As such, combinations of pouches, partitions, dividers, et cetera, can be used to prevent commingling of such products, and/or treatments can be applied to some or all of a pouch to offset the effects of a first consumable or supplement that has an effect on the performance of a second consumable or supplement.

Pouches herein can also include various preservatives or stabilizers for the shelf life or safety of the pouch. These can include antimicrobial agents. Pouches herein can also include agents intended to provide for ease or comfort of use, such as humectants (e.g., glycerol, propylene glycol, alginate, modified starch, hydroxypropyl cellulose, polyethylene glycol (PEG), triacetin, pectin, xanthan gum) or water (or other fluids). Flavors can also be incorporated as treatments or consumables. Various release controlling compositions (including but not limited to magnesium stearate) can also be used to manage the rate or release or uptake of consumables or treatments. pH adjusting agents can be included to assist with the uptake of nicotine or other substances.

FIG. 1 illustrates an example pouch 100 disclosed herein. The pouch 100 can be tubular such that the ends are sealed after filling, can comprise two or more sheets after a consumable is arranged therebetween, or can be constructed in another manner to form an enclosed volume suitable for oral use. In embodiments, pouch 100 can be constructed of a pouch material 110 defining an interior volume 120 containing one or more consumables 130.

The geometry can vary with rounded or squared corners, sides, et cetera. Any geometry capable of enclosing the consumable(s) 130 in a manner exposing surface area to the user's mouth to permit the consumable(s) 130 to be applied to surfaces of the mouth can be used. A pouch 100 can be sealed using, e.g., heat sealing, adhesives, stitching, and other means. The pouch 100 can be made of one or more materials capable of retaining the consumable(s) 130 while allowing some portion of the consumable(s) to pass through (e.g., pouch 100 material is permeable by liquids or solids smaller than a particular size), thereby being absorbed without requiring the user to place the consumable(s) 130 directly in their mouth. Alternatively or complementarily, the pouch 100 can comprise a filter media allowing certain materials to pass through.

Pouches can be formed of one, two, or more materials, and multiple pouches can be used in a single product. Pouch materials can include, but are not limited to, natural or synthetic fabrics incorporating one or more of, e.g., cotton, wool, flax, hemp, ramie, jute, abaca, bamboo, pineapple, wool, silk, wood pulp, other cellulosics, rayon, nylon, polyester, acrylic, microfiber, polypropylene, polymers, et cetera. Pouch materials can be woven or nonwoven; webs of fibers, or contiguous uniform material. Pouch materials can include heat sealable binders, adhesive materials, and/or stitching, which can be incorporated within or separate from a portion of a pouch with which it is or they are used. In embodiments one or more pouch materials can be heat treated or subjected to another process to achieve desired performance or experience (e.g., permeability, strength, moldability, softness, biodegradability, mouthfeel).

Consumables 130 (which can also be referred to as supplements, pouch payloads, or similar terms) can include tobacco, nicotine, nicotine salts, free base nicotine, nicotine provided as a complex between nicotine and an ion exchange resin, such as an ion exchange resin, such as nicotine polacrilex resin, a nicotine inclusion complex or nicotine in any non-covalent binding, nicotine bound to zeolites, nicotine bound to cellulose, such as microcrystalline cellulose, or starch microspheres, and mixtures thereof, coffee, caffeine, CBD, THC, and others. The consumable 130 within the pouch 100 is what the user is seeking to absorb through "dipping.". Consumables 130 can also include materials such as fillers, binders, stabilizers, preservatives, et cetera. The consumable(s) 130 can, in one embodiment, broken up, dissolved, transported, absorbed, et cetera, by saliva or other fluids, such that it can pass through the webs or fibers or be such that it integrates into the saliva and passes through the web or fibers for buccal or sublingual absorption. In embodiments, different formulations or types of consumables can be combined (e.g., in a single consumable composition, in two or more compartments or pouches, as a consumable and a treatment applied to the pouch, et cetera) to provide one or more release profiles to control the rate of release or uptake of a consumable or treatment.

Figure 2:
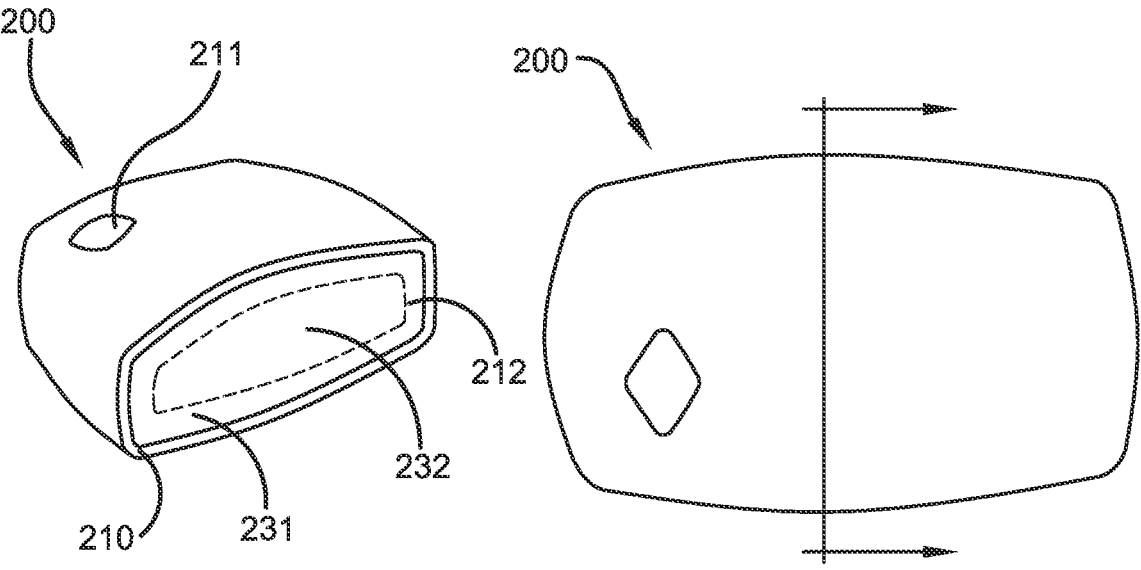
FIG. 2 illustrates an example pouch structure.

FIG. 2 illustrates an example of a pouch 200 incorporating a beneficial health supplement. A pouch can contain a consumable (e.g., nicotine, caffeine, THC, CBD) for use. To add the beneficial health supplement, such as a tooth whitener, oral hygiene product, vitamin or mineral, glucose, medicine, et cetera, a substance containing the beneficial health supplement can be combined with the pouch.

In an embodiment, an applied substance 211 can be applied to at least a portion of the pouch such that the substance is provided to or absorbed by the user orally (e.g., applied to or circulated about one or more of at least one tooth, gums, mouth, throat, et cetera). In an alternative or complementary embodiment, the applied substance 211 can be impregnated into at least a portion of the pouch material such that the substance is provided to or absorbed by the user orally. Such oral use can be passive and require no further action by the user other than using a pouch as normal, e.g., placing the pouch in the user's mouth, under a user's lip, under a user's tongue, in a user's cheek, et cetera.

In embodiments, a health beneficial substance can be combined with the consumable. For example, a tooth whitening substance can be mixed with a nicotine substance and delivered to the user through the pouch material in the same manner as the nicotine.

In alternative or complementary embodiments, a multi-pouch arrangement can be employed, and one or more interior pouches 212 can be arranged within an exterior pouch 210 to achieve aspects disclosed herein. In embodiments, two or more layered pouch materials can provide different filtration effects with respect to the consumables 231 and 232 therein. In embodiments, two or more consumables 231 and 232 can be provided, and separated by an interior pouch 212. For example, a layer of tooth whitening material can be provided about a nicotine pouch 212 whereby an interior nicotine pouch is wrapped by an outer pouch 210 filled with tooth whitener. Alternatively, a tooth whitening interior pouch 212 can be disposed inside an exterior nicotine pouch 210, allowing the nicotine to more rapidly permeate the exterior pouch while providing a different (e.g., slower, longer, more regulated) delivery of the tooth whitening substance. In embodiments, there can be multiple interior pouches 212, either within one another, or disposed side-by-side in the exterior pouch 210. In embodiments one or both of an interior or exterior pouch can be coated or impregnated with a substance 211 (or multiple different substances). In embodiments, an interior pouch 212 can be designed to rupture on pressure (e.g., pinching, chewing, twisting) to mix a first substance 231 within the interior pouch with a second substance 232 within the exterior pouch but not (prior to rupture) within the interior pouch 212. Further, an interior pouch 212 can be designed to controllably release a substance, such as through a user instruction. In one example, the interior pouch 212 can release the consumable 232 at a first rate. However, when the user applies pressure with his or her tongue, the interior pouch 212 releases the consumable 232 at a second rate. In one example, the second rate is greater than the first rate, such as when the substance is a heartburn medicine and the user is experiencing greater heartburn, thus desiring greater medicine for relief. Conversely, in one embodiment, when a user applies pressure with his or her tongue, dispensing the substance can slow or stop, such as when a user has had enough of the substance or is feeling ill effects of the substance.

In embodiments, a substance provided as described herein can have complementary effects to the consumable. For example, various B-vitamins, or other substances that have stimulating effects, or which provoke oral sensations that change the pouch use experience, can be combined with nicotine to change, augment, or supplement the effects felt by the user.

Different or multiple means of providing one or more health beneficial substances with a pouch can be combined in various embodiments. For example, a single health beneficial or complementary substance can be provided using two or more of pouch coating, pouch impregnation, single consumable payload mixing, multiple consumable payloads, et cetera. In another example, two or more health beneficial or complementary substances can be provided using, for each, one or more of pouch coating, pouch impregnation, single consumable payload mixing, multiple consumable payloads, et cetera, and the techniques for providing the two or more health beneficial or complementary substances can be the same or different. Other variants will be understood on review of the disclosures herein.

Figure 3:
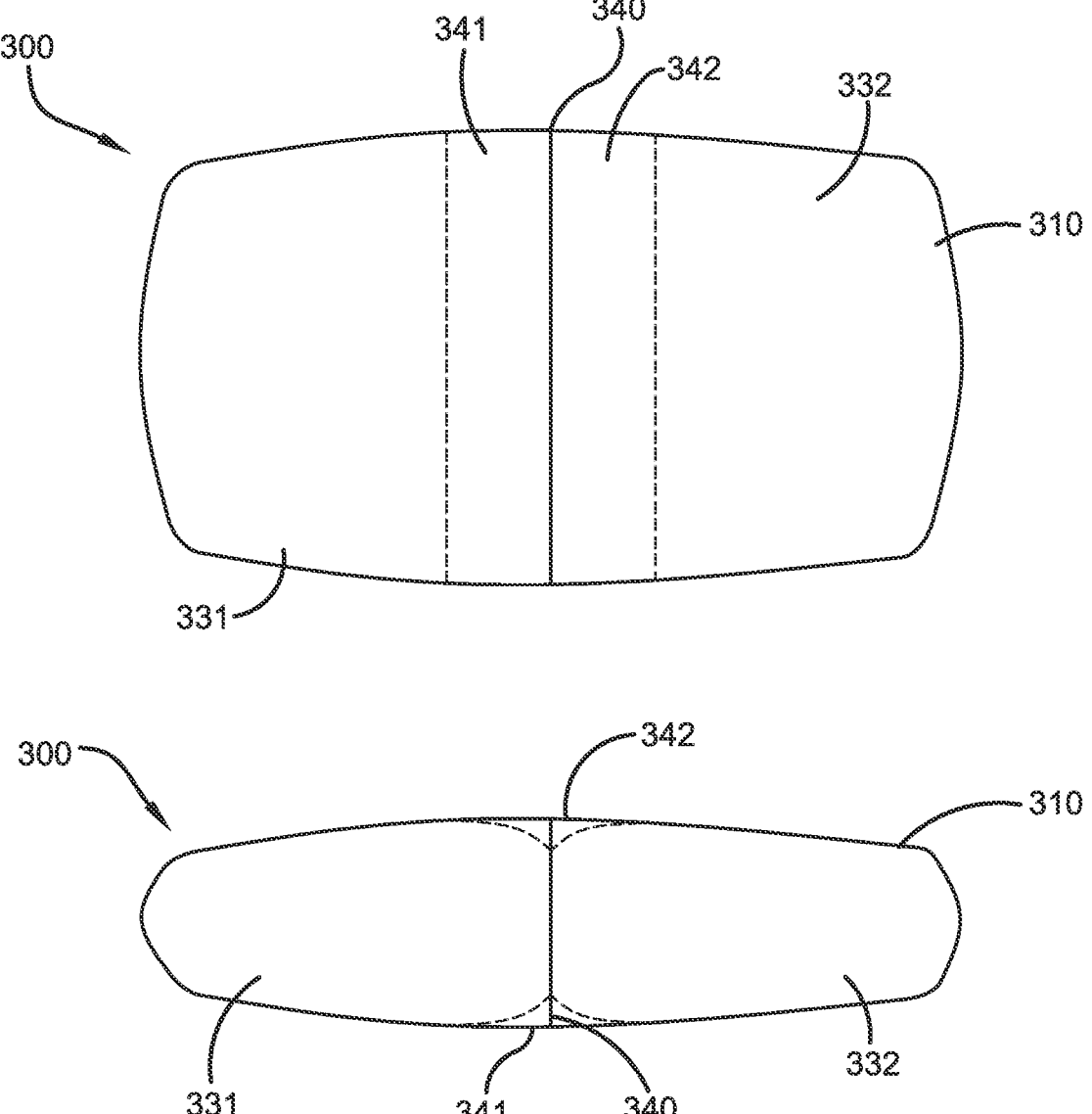
FIG. 3 illustrates an example pouch structure.
Figures 4A, 4B, 4C, 4D, 4E, 4F:
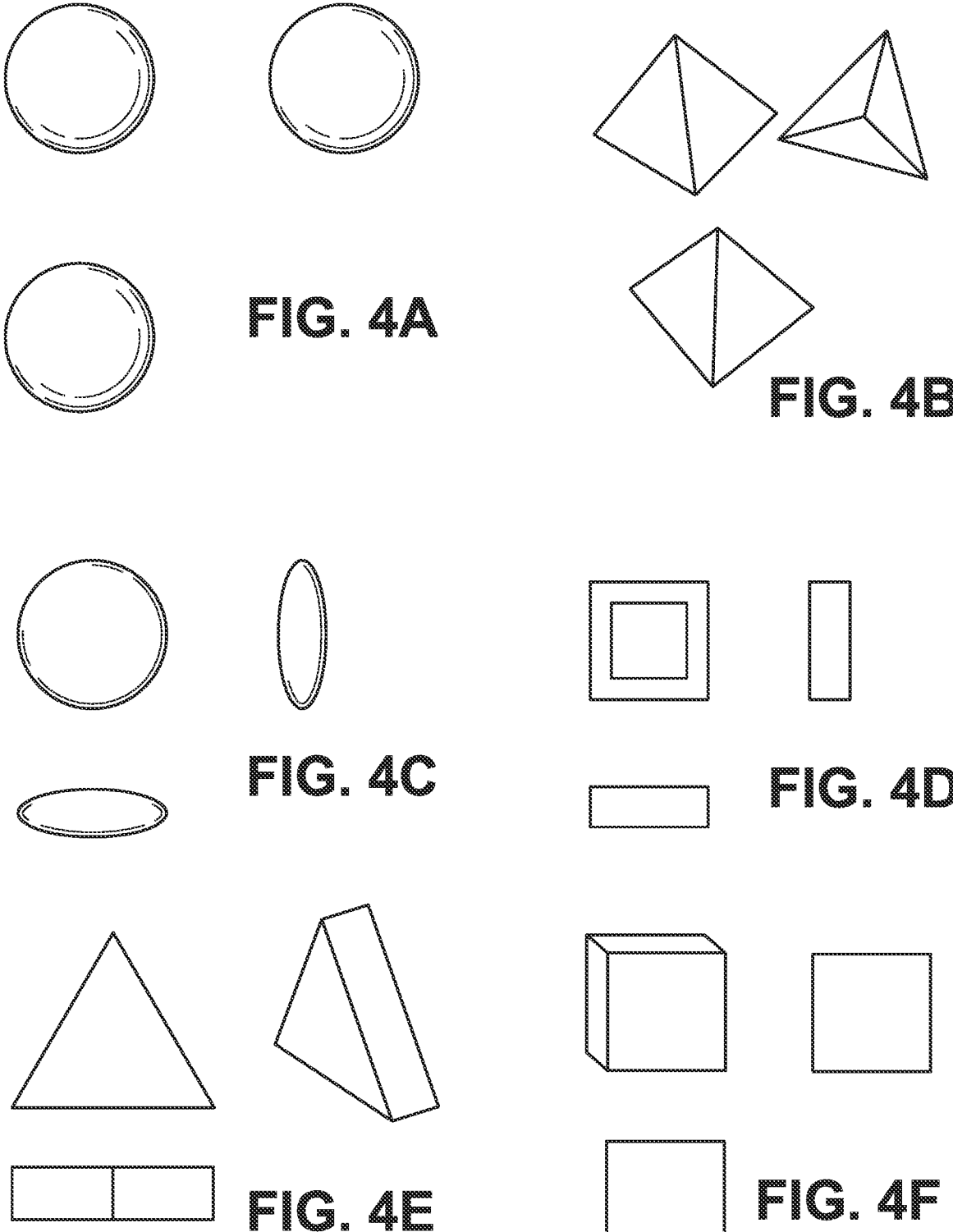
FIG. 4A, FIG. 4B, FIG. 4C, FIG. 4D, FIG. 4E, and FIG. 4F illustrate a variety of alternative pouch structures.

FIG. 3 illustrates another example pouch structure. FIG. 3 shows a pouch 300 formed of pouch material 310 containing a divider 340 to separate compartments or partitions within the pouch. In the illustrated embodiment, divider 340 separates first compartment 331 and second compartment 332, which can contain one or more consumables each, and which may contain different consumables or different consumable composites.

While one divider 300 is shown, multiple dividers 340 can partition pouch 300 into three, four, or more compartments. In embodiments, the compartments can contain different consumables, or two or more compartments can contain the same consumable. In this manner, different consumables can be kept separated until use to prevent commingling.

In embodiments, divider 340 can be formed of an impermeable material. Divider 340 can be flexible. In embodiments, divider 300 can include wrapping extensions 341 and 342. Wrapping extensions 341 and 342 extend the impermeable area of the divider along or around at least a portion of the compartments within pouch 300, further isolating the consumables enclosed within each compartment of pouch 300 by creating a larger gap between surfaces of pouch 300 through which the consumables pass.

In embodiments, a treatment can be applied to one or both sides of the divider. The treatment can be, e.g., another consumable, a substance to enhance the consumable in the compartment it faces, a substance to assist with isolating the consumables in each compartment, et cetera.

While divider 340 is shown substantially centered in pouch 300, it is understood that different compartments defined by divider 340 need not be of equal size, and divider 340 may divide pouch 300 into any proportion. In embodiments, divider 340 can run parallel to the long axis of pouch 300. Moreover, while shown as running essentially along a cross section of pouch 300, divider 340 can be arranged according to any geometries, and can be nonlinear, arranged on angle with respect to any axis of the pouch, et cetera.

In embodiments, different surface treatments can be applied (surface treatment, impregnation, et cetera) to the areas defined by each compartment in a pouch 300 utilizing at least one divider 340. For example, a first substance can be applied to one compartment and no substance is applied to the other, or a first substance can be applied to the pouch portions defining the first compartment and a second substance different rom the first can be applied to the pouch portions defining the second compartment.

While pouch 300 is described as being formed of pouch material 310, in embodiments different portions of pouch 300 can be formed of a different material. For example, a more or less porous material can be used on one side of divider 340, but not the other, to provide for the manner in which the consumable(s) in the respective compartment are absorbed (e.g., allowing more or larger consumable portions to pass through one side than the other).

FIG. 4A, FIG. 4B, FIG. 4C, FIG. 4D, FIG. 4E, and FIG. 4F illustrate alternative geometries for pouches. Examples can include pouches with significant three-dimensional features, such as spherical, pyramidical, or cubic pouches, et cetera. Alternatively, a flatter pouch structures can have, e.g., circular, triangular, rectangular, rectangular, et cetera, profiles. Pouches can vary in size, and can be small, such that multiple pouches fit under a user's lip, or larger, such that a single pouch fills a user's lip or cheek.

A variety of methods provide examples of ways for providing a pouch disclosed herein. Such methods are non-limiting and steps from any method described can be re-ordered, combined with other methods or steps, excluded, et cetera, without departing from the scope or spirit of the disclosure.

In a method, a pouch can be provided. A substance (e.g., a health beneficial substance, a complementary substance) can be coated onto a surface of the pouch. The surface of the pouch can be the surface that contacts the user during use. The surface of the pouch can be the interior surface that does not contact the user during use. In an alternative or complementary embodiment the pouch can be impregnated with the substance. Impregnation can, in embodiments, include soaking the pouch in or wetting the pouch with the substance. Impregnation can include applying the substance to the pouch material before forming the pouch. Impregnation can include applying the substance to a material used to weave or web the pouch material. Impregnation can occur during manufacture of the pouch material (e.g., mixed into polymer, mixed with pulp, applied to or bonded with fibers or other material before further processing, et cetera).

Figure 5:
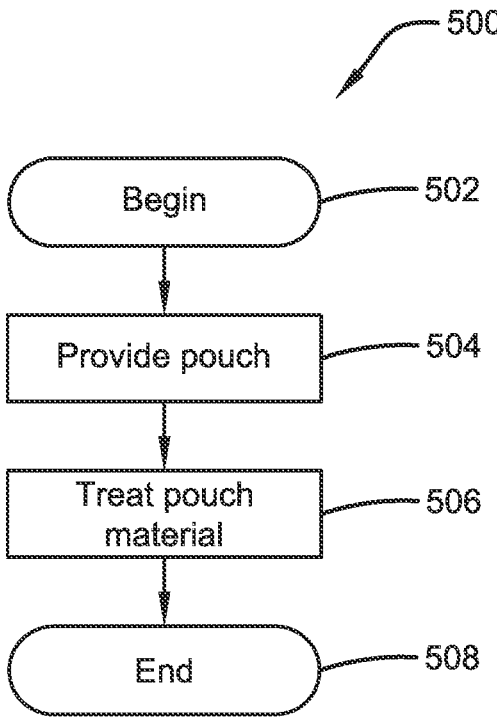
FIG. 5 illustrates an example method for producing a pouch.

FIG. 5 illustrates an example methodology 500 for providing a pouch treated with a consumable or supplement in addition to containing a consumable within the pouch.

Method 500 begins at 502 and proceeds to 504 where a pouch is provided. The pouch can be formed of any appropriate material including any material described herein. The pouch can be a pouch defining a single compartment, or it may be a pouch including a divider forming multiple compartments, and/or it may contain other pouches, or it may take any other embodiment or combination of embodiments described herein.

At 506 the pouch can be treated. Treating can include, e.g., coating the pouch material, impregnating the pouch material, soaking and drying the pouch material, adhering the pouch material, et cetera, using a substance that can be the same or different from the consumable or supplement within the pouch's at least one compartment. In embodiments, different treatments can be applied to different parts of the pouch (e.g., different sides of the pouch, areas around different compartments or portions thereof, interior or exterior, combinations thereof). After treating the pouch material, methodology 500 can end at 508.

Figure 6:
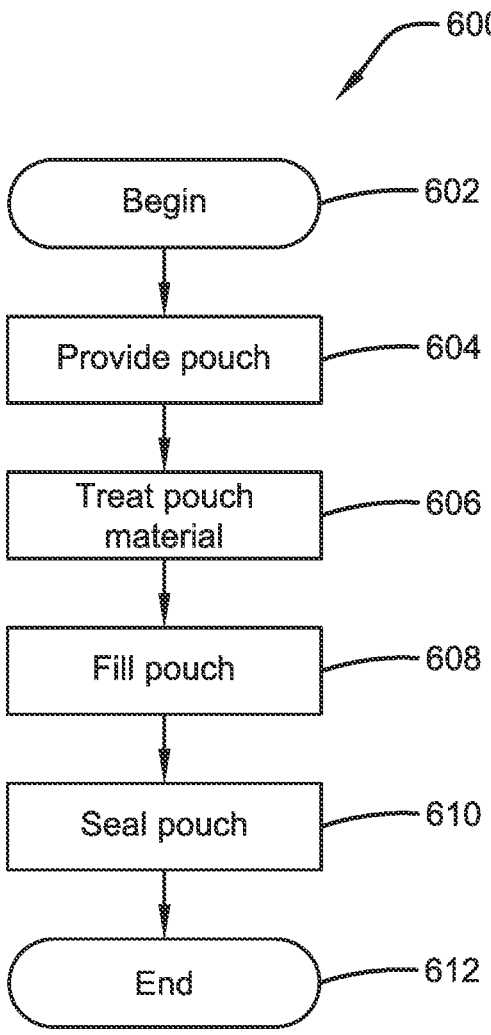
FIG. 6 illustrates an example method for producing a pouch.

FIG. 6 illustrates an example methodology 600. Methodology 600 begins at 602 and a pouch is provided at 604. At 606 a pouch can be a treatment can be applied to the pouch. At 608, a pouch can be filled with one or more consumables. In embodiments, the pouch can also be filled with other substances as discussed herein. Thereafter, at 610, the pouch can be sealed. Sealing can include one or more of, e.g., heat fusing, stitching or weaving, adhering, additive manufacturing techniques, et cetera. At 612, methodology 600 ends.

Figure 7:
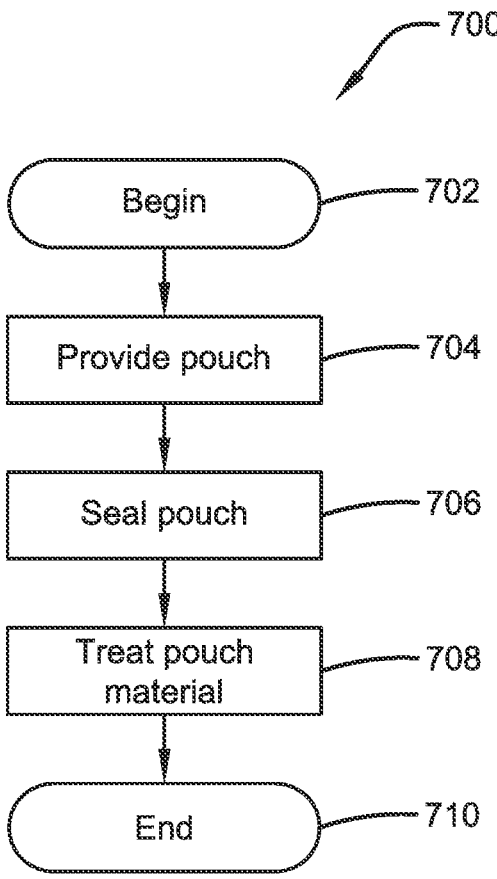
FIG. 7 illustrates an example method for producing a pouch.

FIG. 7 illustrates an example methodology 700. Methodology 700 begins at 702 and proceeds to 704 where a pouch is provided. The pouch can be provided with consumables and/or other substances, or filled after providing. At 706, the pouch can be sealed. In methodology 700, at 708 a treatment is applied to the pouch after sealing. Methodology 700 can thereafter end at 710.

Figure 8:
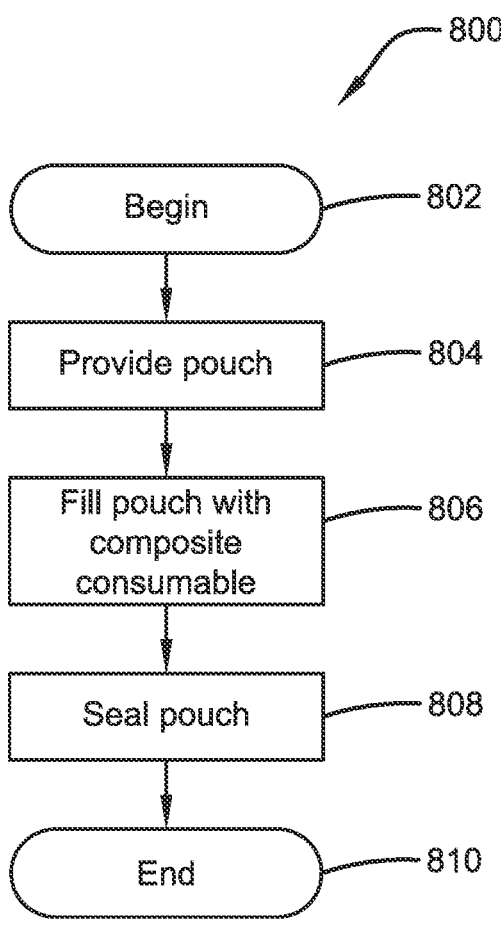
FIG. 8 illustrates an example method for producing a pouch with a composite consumable.

FIG. 8 illustrates an example methodology 800. Methodology 800 begins at 802 and proceeds to 804 where a pouch is provided. At 806 the pouch can be filled with a composite consumable of two or more consumables and/or various other substances described herein. At 806 the pouch can be sealed and methodology Boo ends at 810.

Figure 9:
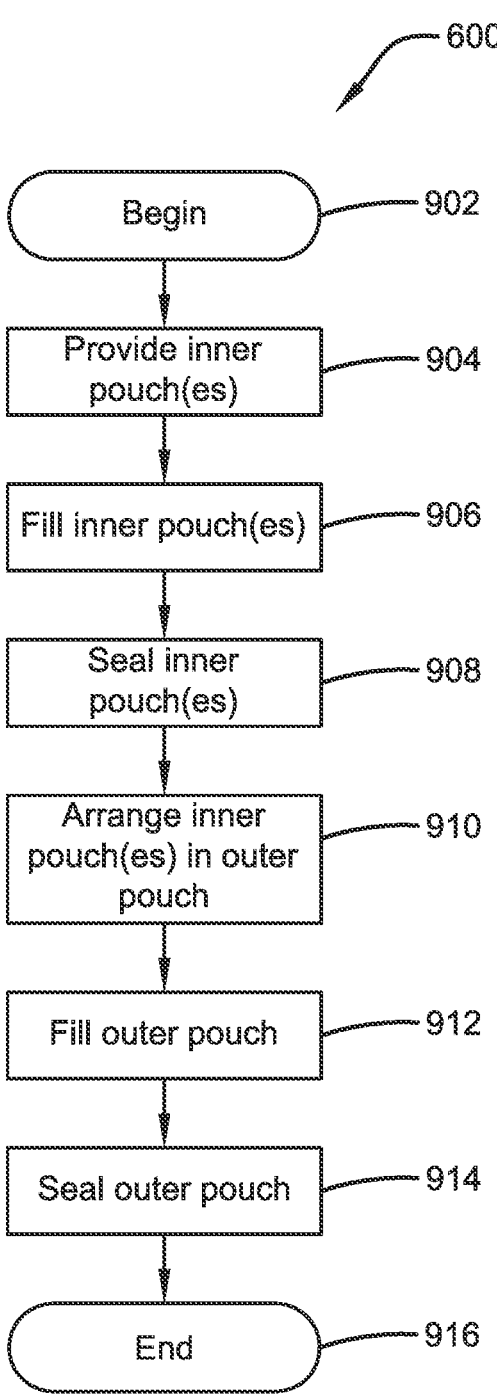
FIG. 9 illustrates an example method for producing a pouch containing at least one inner pouch.

FIG. 9 illustrates an example methodology 900. Methodology 900 begins at 902 and proceeds to 904 where an inner pouch is provided. The inner pouch can be filled with consumable(s) or other substances at 906. Inner pouch can be treated before or after filling, or not treated. At 908, the inner pouch can be sealed, and at 910 inner pouch can be arranged inside an outer pouch. At 912 the outer pouch can be filled around or over the inner pouch. At 914 the outer pouch can be sealed. The outer pouch can be treated before or after filling and/or before or after filling or arranging the inner pouch. Methodology 900 can end at 916. In embodiments, two or more inner pouches can be included in a single product.

Figure 10:
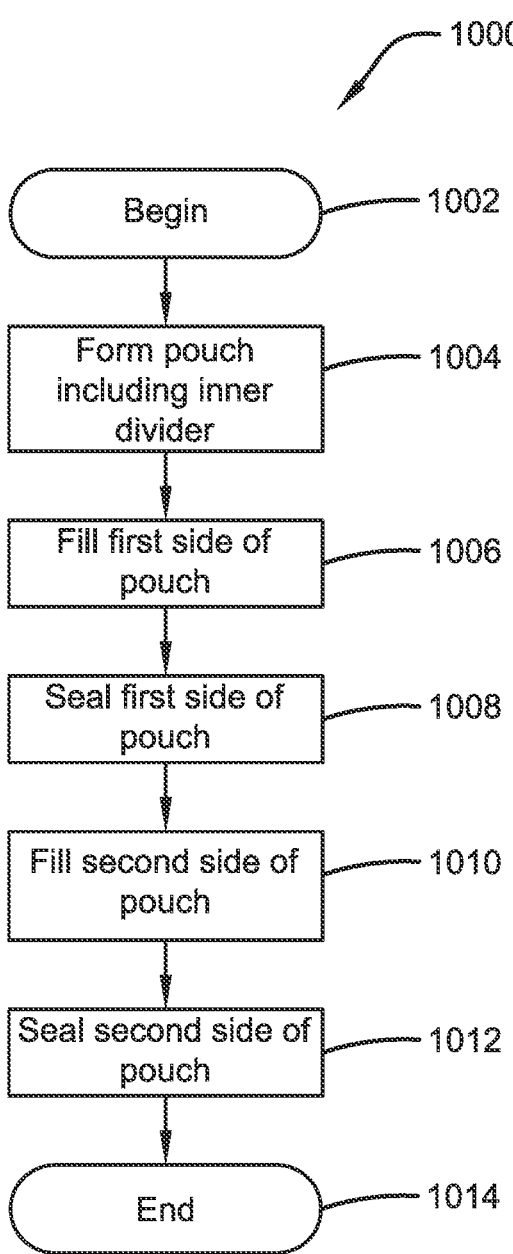
FIG. 10 illustrates an example method for producing a pouch with a divider.

FIG. 10 illustrates an example methodology 1000. Methodology woo begins at 10002 and proceeds to 1004 where a divider is formed or arranged within the pouch. The divider can be formed during construction with the pouch or arranged therein and attached by any means described herein. At 1006, a first side of the pouch can be filled with one or more consumable(s) and/or one or more other substances described herein. Methodology 600 illustrates another method disclosed herein. In alternative embodiments, the first side of the pouch can be filled before creating or inserting the divider. At 1010, the second side of the pouch can be filled with one or more consumable(s) and/or one or more other substances described herein. Thereafter, at

1012, the second side of the pouch can be sealed. The pouch, or any portion thereof, can be treated as described herein. At 1014, methodology woo can end. In embodiments, methodology woo can include multiple dividers, defining three or more compartments, without departing from the scope or spirit of the innovation.

The methodologies described herein can be various combined or mixed-and-matched, or steps can be performed in different orders or repeated, or steps can occur concurrently, without departing from the scope or spirit of the innovation. In one embodiment, a pouch can be packaged without any additional substance. A packaging, along with the pouch or separate, a number of vats of substances can be provided to the user. The user can select the substance by soaking the pouch. As examples, when the pouch is a medicine various flavors can be provided or when the pouch is a tobacco product, the user can select between teeth whitening and/or anti-heartburn based on the user's experience with using the tobacco product.

In embodiments, the pouch can be coated and/or impregnated with the substance before filling and sealing the pouch.

In embodiments, the pouch can be filled and sealed before being coated or impregnated with the substance.

In embodiments, the pouch can be filled with a composite consumable (e.g., including the substance) before sealing.

In embodiments, an inner pouch can contain, be coated with, or be impregnated with the substance before being placed into an outer pouch for sealing.

In embodiments, an outer pouch can be filled with, coated with, or impregnated with the substance. This can occur before or after at least one inner pouch is arranged therein, and, for coating or impregnation, before or after sealing the outer pouch.

In embodiments, multiple techniques for providing one, or two, or more substances with the consumable (e.g., nicotine, caffeine, THC, CBD) can be combined, i.e., one or more composite consumables, one or more coatings or impregnations, one or more interior pouches, et cetera, can be used in a single pouch.

In one embodiment, the pouch can contain a sensor that can remotely communicate with an electronic device, such as a smartphone or health tracking app. As previously stated, the pouch can deliver medicine to an unconscious patient or vitamins to provide the health of a user. Amounts of medicine, vitamins, or the like delivered to a user can be tracked by the sensor and sent to the electronic device for recording. Based on this, the next dosage can be determined such as by a medical professional or algorithm.

Conversely, and as previously stated, a user can employ the pouch disclosed herein to assist in quitting tobacco usage. The sensor can record how much tobacco or nicotine the user has used in a given period of time, such as in the last 24 hours. Based on this, the electronic device can suggest how much tobacco the user should use over the next 24 hours, such as determined through an algorithm (e.g., based on feedback from the user on cravings, aggregated feedback from users of an app, et cetera). The ultimate goal of this tracking is to allow the user to use less and less tobacco until the user stops.

Moreover, there can be safety aspects integrated with the electronic device. For example, while a teeth whitening chemical can be beneficial in regular doses, too much may be harmful either to teeth or have other negative health consequences. The electronic device can track how many pouches a user used in a time period, such as a week long period, and if a threshold is exceeded the user can receive a notification by way of the electronic device and/or a communication can be sent to the pouch to deactivate release of the medicine.

A similar situation can occur with someone trying to quit using tobacco, the user can try to use more pouches in a day than allotted for someone trying to quit. The electronic device can communicate to the sensor that tobacco should not be released. In one example, the pouch can have multiple chambers with an inner chamber surrounded by an outer chamber. When a signal is received, the inner chamber breaks allowing tobacco to be accessed by the outer chamber and thus usable by the user. If the signal is not received, then no tobacco is released and the user does not use more tobacco (e.g., a placebo can be provided for the user between the inner chamber and outer chamber). A sensor in the pouch can be activated when entering a mouth (e.g., the outer pouch gets wet from saliva and the sensor senses this). This activation can cause a request signal to be sent to the electronic device and without a response approval signal the inner chamber does not give access to the tobacco.

Figure 11:
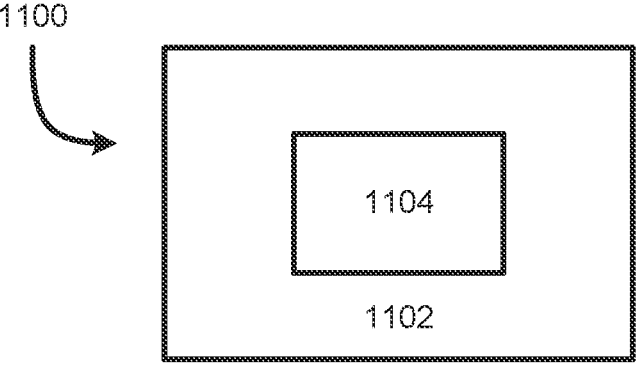
FIG. 11 illustrates an example pouch including an electronic component.

FIG. 11 illustrates a system 1100 in which an example pouch 1102 includes an electronic component 1104. Electronic component 1104 can include, but need not be limited to, one or more of a sensor, a transmitter, a computer-readable medium, a radio frequency identification tag or other transponder (including various passive transponders). System 1100 can be utilized to track types and amounts of consumables or other substances in various pouches. In embodiments, an electronic component 1104 can be detected or emit when, e.g., pouch 1102 is taken out of a container, pouch 1102 is moistened, consumables or other substances in pouch 1102 are released, et cetera. In embodiments, electronic component 1104 can transmit or be interrogated to provide details on length of use, amount of consumables or other substances released, aggregate amounts of consumables or substances based on the use of multiple pouches in a given time period, et cetera. Pouch 1102 can interact with another system including, e.g., a processor, computer-readable medium, computer-readable instructions (including but not limited to, e.g., an "app") to provide various functionality relating to pouch usage, tracking, et cetera.

While aspects herein predominantly relate to pouches, it is understood that aspects providing health benefit could be integrated with gums, lozenges, and other products without departing from the scope or spirit of the innovation. In embodiments, a tray or strip can be provided to apply the consumable and health beneficial or complementary substances as a gel in the mouth. The tray can include light or laser emitters to act as a light-based activator. In embodiments, consumables or supplements described herein can be mixed with loose oral products (e.g., long cut tobacco, snuff, powder, paste, other products).

Terms herein may include examples used to explain features of terms and are not intended to be limiting. In addition, where a singular term is disclosed, it is to be appreciated that plural terms are also covered by the definitions. Conversely, where a plural term is disclosed, it is to be appreciated that a singular term is also covered by the definition. In addition, a set can include one or more member(s).

References to "at least one embodiment", "one embodiment", "an embodiment", "one example", "an example", and so on, indicate that the embodiment(s) or example(s) so described may include a particular feature. The embodiment(s) or example(s) are shown to highlight one feature and no inference should be drawn that every embodiment necessarily includes that feature. Multiple usages of the phrase "in at least one embodiment" and others do not necessarily refer to the same embodiment; however this term may refer to the same embodiment. It is to be appreciated that multiple examples and/or embodiments may be combined together to form another embodiment. Where lists of samples or embodiments are provided, such lists are not intended to be exhaustive listings, but rather provide one of ordinary skill in the art with a conceptual framework to understand various possibilities or classes to be applied in the situation including options that may not be expressly listed.

What is claimed is:

1. A product, comprising:

a saliva-permeable pouch;

a nicotine consumable arranged in the saliva-permeable pouch, wherein at least a portion of the nicotine consumable passes through the saliva-permeable pouch when the pouch is moistened; and a tooth-whitening substance, wherein the tooth-whitening substance has a neutral or alkaline pH.

2. The product of claim 1, wherein the tooth-whitening substance is combined with the nicotine consumable in the pouch.

3. The product of claim 1, wherein the tooth-whitening substance is applied to a material of the saliva-permeable pouch.

4. The product of claim 1, wherein the tooth-whitening substance is impregnated into a material of the saliva-permeable pouch.

5. The product of claim 1, comprising:

a divider within the saliva-permeable pouch configured to define a first compartment and a second compartment within the saliva-permeable pouch, wherein the nicotine consumable is arranged in the first compartment and the tooth-whitening substance is arranged in the second compartment.

6. The product of claim 1, comprising:

an interior pouch disposed within the saliva-permeable pouch, wherein the interior pouch is also saliva-permeable, and wherein the tooth-whitening substance is enclosed within the interior pouch.

7. The product of claim 1, comprising:

a desensitizing agent, wherein the desensitizing agent has a neutral or alkaline pH.

8. The product of claim 7, wherein the desensitizing agent is applied to a material of the saliva-permeable pouch.

9. The product of claim 7, wherein the desensitizing agent is impregnated into a material of the saliva-permeable pouch.

10. The product of claim 1, comprising:

one or more vitamins.

11. The product of claim 1, comprising:

one or more medicines.

* * * * *